(12) United States Patent
Cecchi

(10) Patent No.: US 7,943,293 B2
(45) Date of Patent: May 17, 2011

(54) MEDIA SOLUTIONS AND METHODS FOR CRYOPRESERVATION AND THAWING OF IN VITRO FERTILIZATION SPECIMENS

(75) Inventor: Michael D. Cecchi, Madison, CT (US)

(73) Assignee: Genx International, Inc., Guilford, CT (US)

( * ) Notice: Subject to any disclaimer, the term of this patent is extended or adjusted under 35 U.S.C. 154(b) by 72 days.

(21) Appl. No.: 12/454,942

(22) Filed: May 27, 2009

(65) Prior Publication Data

US 2009/0298044 A1    Dec. 3, 2009

Related U.S. Application Data

(60) Provisional application No. 61/130,058, filed on May 28, 2008.

(51) Int. Cl.
*A01N 1/00* (2006.01)
*C12N 5/00* (2006.01)

(52) U.S. Cl. .................................. 435/1.3; 435/325
(58) Field of Classification Search ............... 435/1.3, 435/325
See application file for complete search history.

*Primary Examiner* — Deborah Crouch
*Assistant Examiner* — Marcia S Noble
(74) *Attorney, Agent, or Firm* — William W. Jones

(57) ABSTRACT

A medium solution which will increase the growth, survival and ultimately the live birth rate of oocytes and embryos which have been or will be subjected to cryopreservation. The solution contains varied amounts of glucose, pyruvates, amino acids, vitamins K5 and C, antioxidants, fatty acids to supply the specimens with the chemical ingredients and uptake requirements required to recover and prosper during and after the cryopreservation process. The solution supplies nutrients to the specimens that will replenish depletion and damage to the specimens and their mitochondria, spindles and structural features, such as cell walls. One formulation addresses the additional requirements of frozen specimens as opposed to the current media solutions and methods which treat the un-frozen specimens the same as the frozen specimens when recovering them from cryopreservation.

5 Claims, 2 Drawing Sheets

MEDIA SOLUTIONS AND METHODS FOR CRYOPRESERVATION AND THAWING OF IN VITRO FERTILIZATION SPECIMENS

This application claims the benefit of Provisional Patent Application Ser. No. 61/130,058, filed May 28, 2008.

FIELD OF THE INVENTION

Media solutions and methods of using the same for the restoration, resuscitation and treatment of oocytes, embryos and stem cells before and after after cryopreservation or vitrification.

BACKGROUND OF THE RELATED ART

Human and other animal cells are presently being frozen, stored, and then thawed as a means of saving these materials for use at a later date. Currently, human embryos are frozen and/or vitrified to accomplish cryopreservation. The terms frozen, vitrification and cryopreservation are interchangeable for the purpose of the subject disclosure.

The problem facing current methods of cryopreservation is the recovering process and then the culturing to implantation for oocyte and embryos, and the resulting actual live birth. Currently, the freezing and thawing of a human oocyte may result in approximately a 10% overall live birth rate, which is well below the actual live birth rate of non-frozen oocyte or embryos. The conditions affecting the oocyte also affect embryos which are frozen and thawed and then implanted. In other words, there is a reduced rate of live birth for the frozen embryos as compared to the non-frozen embryos.

The prior methods for the preparation and cryopreservation of specimens such as embryos, oocyte and stem cells are centered on separate and different solutions and chemical ingredients.

When the time comes to thaw the specimens the current methods utilize a progression of media that contain a combination of solutions used in sequence. Again one may use up to seven different media solutions that are in separate vials. The more common methods are a progression of media reducing the level of sucrose in each and then the last solution will be sucrose free and used for washing. After a specimen is thawed it is then transferred into a generic solution or off the shelf culture media solution used for the normal culturing of oocyte and embryos and do not address any changes in concentrations or the addition of new ingredients to compensate for the freezing and thawing process.

In the current methods of cryopreservation, the specimen is immersed into a series of media and cryoprotectorants whereby the concentration of the cryoprotectorants (CP) is increased until, in some methods, the CP is 50% of the solution. The resulting infusion of the CP into the cells displaces water in the cells and dehydrates the cells during this introduction of the CP. This can be harmful to the cells. The cells are then vitrified and then plunged into liquid nitrogen (LN) at a temperature as low as −180 C. The specimens will then be stored in the LN until they are to be used.

The specimens, when needed, are removed from the LN and then immersed in a series of media used to thaw the specimens. Currently, most of these media contain a solution consisting of a base saline medium, HSA (10-20% of solution) and sucrose as an energy source. In one example Vial #1 will contain 0.85 mM of sucrose. Vials #2 through #4 will decrease the sucrose concentrations stepwise down to 0.10 mM in Vial #4, and then Vial #5 will contain only a base media and HSA, and no sucrose.

The specimens will then be placed into a "generic" culture media until usage. Embryos will be held in this medium until they are transferred into the patient. Currently, embryos used in human IVF will be immersed in several media, embryo culture media, such as P1, HTF, HTF w/SSS and Irvine ECM® (Irvine Scientific), G2.2 through G5 series (Vitrolife), Quinn's Advantage (Sage), Cook® Cleavage and Cook® Blastocyst (Cook IVF), Universal IVF medium®, EmbryoAssist™, BlastAssist™, ISM1 and 2™ and others (MediCult), Sigma Ham's F-10 and MEM 199 (Sigma), and Global® (LifeGlobal). These media have not been modified to accommodate the problems being faced by the specimens in their post thawing development. They are not modified to be different for nonfrozen embryos as differentiated from frozen and then thawed embryos.

The introduction of the CP in the freezing process often results in problems with and damage to the cells, such as dehydration, membrane damage, damage to the spindle, DNA damage, alterations to proteins, stripping of proteins, may alter ingredients, as well as other structural and physical changes and damage. For example, the frozen state can result in damage to the cell walls and to the mitochondria.

The freezing process may introduce other factors such as ice formation during either cooling or warming, and mechanical disruption of cells contributing to the destabilization of membranes. Severe dehydration from the exposure to concentrated CP can cause the structural transitions of biological molecules including lipids and proteins.

It appears that oocytes and embryos may lose or have certain diminished metabolic levels within the oocytes or embryos after the current freezing and thawing procedures, and the current practices do not address these freeze related extractions of certain proteins or nutrients when the CP is extracted or added.

The problems facing the specimens is that they may not recover from the freeze, may not be fully flushed of the cryoprotectorant, may have suffered physical damage to membranes or mitochondria and may not be provided with the correct dosage of the required nutrients or ingredients in order to recover. The problem facing the specimens is that most media used in the freezing and thawing processes are those "generic" media which are used for the culture and development of nonfrozen specimens, and which have different requirements.

In the current methods used for cryopreservation techniques, the specimens are not "cultured" or "aided" in the process when they are going to be placed into cryopreservation or thawed out of cryopreservation. The users utilize "generic" media, as they do in post thawing, as mentioned earlier, and do not add or alter any ingredients which may better prepare the specimen for cryopreservation, thawing or recovery.

The specimens are placed into vitrification kits, which do not address pre-vitrification or post vitrification conditions. Currently, embryos used in human IVF will be immersed in several vitrification solutions as part of a sequential kit, such as Embryo and Blastocyst Freeze and Thaw Kit, Blastocyst Vitrification Freeze and Thaw and others (Irvine Scientific), G-FreezeKit Blast™, RapidVit™ Cleave, RapidWarm™ Cleave and others (Vitrolife), Quinn's Advantage® embryo freeze kit, Quinn's Advantage® blastocyst freeze kit (Sage), Blastocyst Cryopreservation™ and Blastocyst Vitrification™ (Cook IVF), OocyteFreeze™ and Thaw™, BlastFreeze™ and BlastThaw™ and others (MediCult). These vitrification solutions, used in sequence do not contain a solution or method of immersing the embryos in a specially prepared, modified media to accommodate the problems being faced by the specimens of their pre-vitrification or post thawing procedures. They do not modify the media, solutions or methods so as to be different for nonfrozen embryos as differentiated from frozen, and then thawed, embryos.

SUMMARY OF THE INVENTION

The subject invention relates to methods and culture media which will assist and enhance the rehabilitation, recovery and growth of specimens such as embryos, oocytes and stem cells after they have been subjected to a vitrification or freezing process, and subsequently thawed, and will provide important enhancements and ingredients to the specimens, which will allow them to recover, rebuild, and grow to the implantation stage and, in the case of embryos, result in increased live births. The subject invention helps to correct changes and deficiencies created during the preparation for freezing, the actual freezing process and deficiencies which will be mitigated during the thawing or warming of the specimens.

The media and methods of this invention better provides the specimens with necessary ingredients at various levels of concentration to give each specimen a better chance for recovery, survival, rebuilding and ultimately live births in the case of embryo specimens. The subject invention addresses changes, the depletion of certain chemicals and structural alterations, and damage resulting from the cryopreservation process.

The adaptation of a medium to become a recovery medium will require the altering or adding of certain ingredients such as glucose, pyruvate and lactate, fatty acids, such as lipoic and linoleic acids, antioxidants, such as alpha tocopherol acetate (Vit. E) and ascorbic acid (Vit. C). Vitamins such as C and K, may contain cysteamine and chelators, such as EDTA, alpha and beta globulins and gamma globulin. Therefore most other media may already exceed the amount of glucose to be used and do not have the same ratios as this invention's composition has, after the changes. The problem facing most common media is their inability to establish the same ratios of glucose, lactate and pyruvate, fatty acids, antioxidants, vitamins and alpha and beta globulins and gamma globulin, without affecting the remaining ingredients. Vitamin K5 is one of the K vitamins which is suitable for use in the medium of this invention.

The adaptation of the media to be used inside or outside the incubator would greatly benefit the specimens. By including or not including HEPES or MOPS, bicarbonate buffers, would give these special media solutions the ability to be used in both the thawing process and culturing process. Making the special media solutions available, without HEPES, allows the extended culturing of the specimens, and by adding HEPES or MOPS allows the media to be used outside the incubator as most of the thawing protocols call for.

It would be highly desirable to provide media solution that would provide thawing and post thawing embryos, oocytes and stem cells with ingredients that will aid in the recovery process and to repair conditions that are a result of cryopreservation preparation, freezing and thawing.

It would be highly desirable to provide a media that replenishes energy sources, proteins and repair membrane damage of the specimen which were altered, stripped or damaged during the CP process.

It would be highly desirable to provide a media solution which will aid in the recovery and repair process of cells, oocyte, embryos and stem cells and result in a higher recovery and useful rate and in the case of oocyte and embryos increase the live birth rate.

It should be appreciated that the present invention can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the following drawings.

DETAILED DESCRIPTION OF THE INVENTION

Many of the ingredients of the media of this invention have an impact, some being glucose, pyruvates and lactates, fats, vitamins, proteins and antioxidants, Amino acid concentrations are also needed in order to provide for the synthetic requirement of cellular repair. When the time comes to be revived or unfrozen, the specimen is then removed from the liquid nitrogen container and placed into a series of thawing media for a specific time intervals and through several steps.

The method and system of this invention will provide pre-vitrification, thawing and post thawing embryos a balance of ingredients that will provide the embryo with those ingredients which will allow it to better recover from a metabolic shift and inner mitochondrial membrane damage caused by the CP process. When the specimens are being prepared for cryopreservation the specimens are handled in several different methods and different ingredients, depending on the selected protocols and products. The subject technology will increase the chances of increased pregnancies and live child birth in the embryos cultured in the solution as opposed to the other solutions. The subject technology will increase the chances of stem cells recovering and becoming more useful as well a greater survival rate. Some of the combinations will include ingredients such as stabilizers or antifreeze proteins which may help recovery and development. The subject disclosure may include energy sources such as fructose, glucose, maltose, mannitol, sorbitol, sucrose and trehalose. Additional ingredients such as, vitamins fats, globulin and antioxidants are included. The subject disclosure has also altered the volume of calcium, magnesium and phosphate to help support development.

Figure 1:
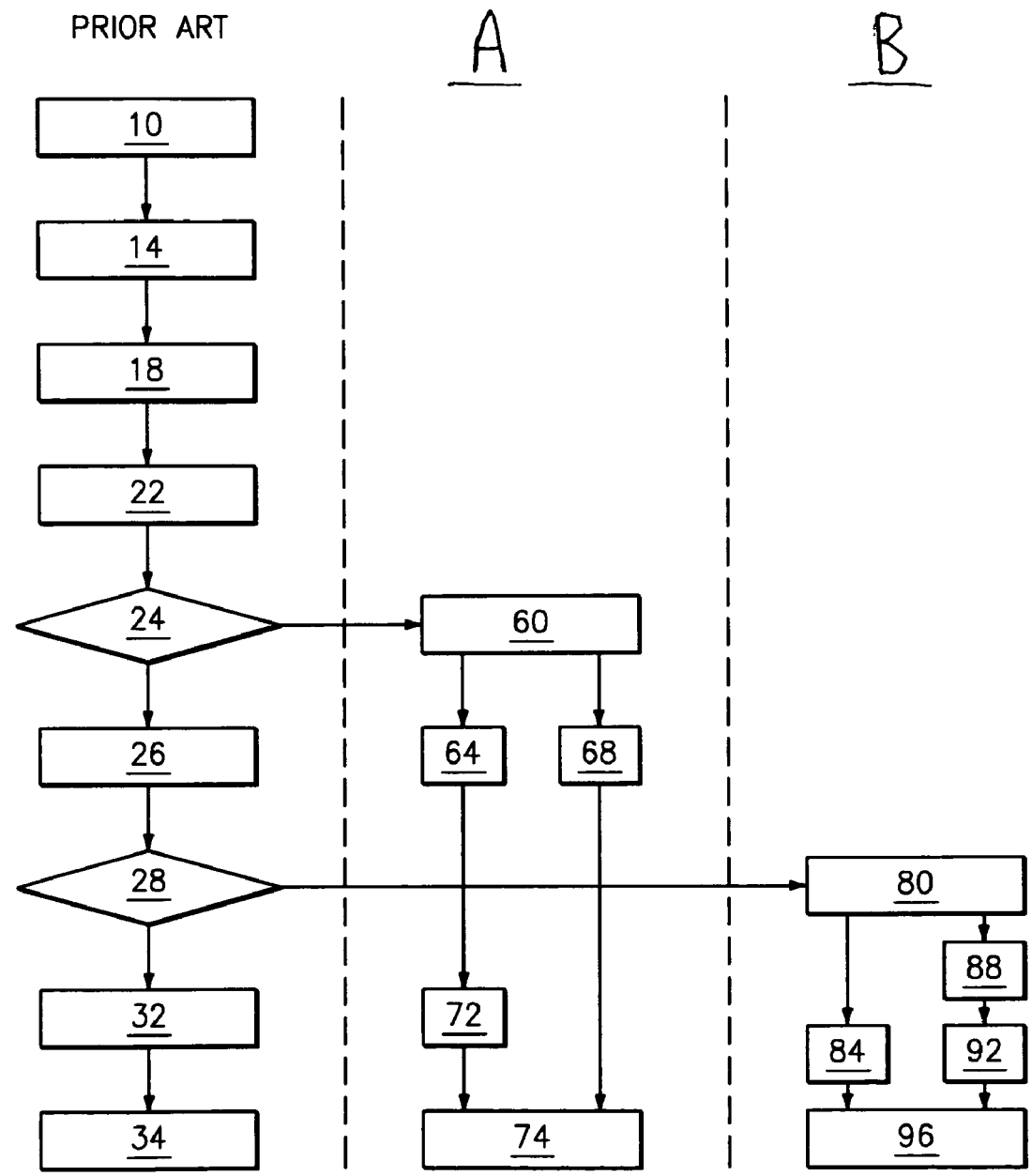
FIG. 1 is a flow chart showing methods for application of the invention in an embryo thawing process.

Referring now to the drawings, FIG. 1 compares current methods of thawing or devitrifying specimens with an embodiment of the invention and its methods for thawing and devitrifying. It further describes the current methods for the thawing and use of the specimens, compared to the new method. In this example embryos are used as the specimen, the methods of thawing them, placing them in media solutions until they are ready for transfer and then the transfer step. It will be appreciated that embryos, stem cells and oocytes can be treated in a similar manner by using the resuscitation solution of this invention. Current methods may use from 2 to 7 vials in the thawing process, and may vary in the times. For this example we are describing a method using 4 thawing steps and 4 separate solutions the specimens remain in each solution. In this example the fourth vial is considered the last step.

In this example the frozen embryos are removed from the liquid nitrogen tank 10 and placed into the first thawing solution 14. Current media will consist of a base media solution, which will include from 0.5-0.8 mM of sucrose and 10-12 mg/ml of Human serum albumin (HSA) and may contain 1,2propandiol or similar cryoprotectorants. The ingredients may vary, but are fairly consistent through the many manufacturers. The embryo remains in the first solution 14 for approximately 5 minutes. The embryo is then transferred to vial #2 18 for 5 minutes. Vial #2 18 may contain a base media, from 0.2-0.5 mM of sucrose and HSA and may contain 1,2propandiol or similar cryoprotectorants. The embryo is then moved into the Vial #3 solution 22 for approximately 10 minutes. Vial #3 22 may contain a base media, from 0.1-0.2 mM of sucrose and HSA. The embryo is then moved to a generic media 32, for several hours and then transferred into the patient. In this example "generic media" refers to a media that is used for un-frozen specimens and is not differentiated for frozen specimens. The embryos are then moved from the generic media 32 and transferred into the patient 34.

In practicing the method of this invention, the user may use the current methods of moving the embryos through the 1st solution 14, second solution 18 and the 3rd solution 22. The embryos are removed from the #3 thawing solution 22 and at step 24 moved to the rejuvenating solution 60 of this invention. The solution 60 is a solution which addresses the needs of embryos that were frozen and are being thawed to be later implanted, and addresses the fact that the frozen embryos have different nutritional needs than fresh embryos. In Method A the embryos are moved at 24 into the solution 60 before they are put into the last thawing solution 30. This exposes the embryos to the enhancements of the solution 60, due in part to the fact that most last thawing solution are only a base media solution and HSA (human serum albumin). Therefore it is more beneficial to be in the solution 60 than in the last solution 26. This example also allows the solution 60 to become the final solution used in the sequence of solutions and the last solution in kits currently provided by IVF companies.

In Method A, the embryos are held in the solution 60 for a period of time, undefined in this example, and then may be moved in step 64 to a "generic medium" 72 for a predetermined period of time. The embryos are then transferred to the patient 74 from the generic medium 72. This allows users to use any of a number of generic media that they may be more accustomed to before they transfer the embryo. The embryo is then moved from 72 and transferred into the patient 74.

Alternatively in Method A, the embryos may be held in the solution 60 until they are transferred into the patient 76, through step 68. Therefore this embodiment is a unique combination of steps and is used in the thawing and recovery process of the embryos as well as used for the growth and culturing of the embryos through to the transfer stage 74.

In Method B, the embryos are placed in the Method B last solution 30, then at step 28 are moved to the rejuvenation solution 80. The move to the solution 80, in this example, allows the user to utilize the steps or protocols of the current method, which are steps or protocols they may prefer, or be more accustomed to using.

After the embryos are moved to the solution 80, they may be cultured in the solution 80 (step 84) until they are transferred into the patient 96. The user may choose to move the embryos in step 88 to a generic medium 92, for a time period, a step which they may be more accustomed to, and then the embryos can be implanted into the patient 96.

In this example the media solutions of 32, 72 and 92 may be generic medium, may be a "transfer" medium, or may be a combination of both. Transfer medium, in this example, is a medium designed for the step of transferring the embryo to the patient and may include additional ingredients, such as hyaluronic acid. This example demonstrates the unique nature of the rejuvenation solution, and its added specific ingredients and the old Methods A and B, for the handling of the embryos and the introduction or addition of the rejuvenation solution into the older current methods and protocols.

Figure 2:
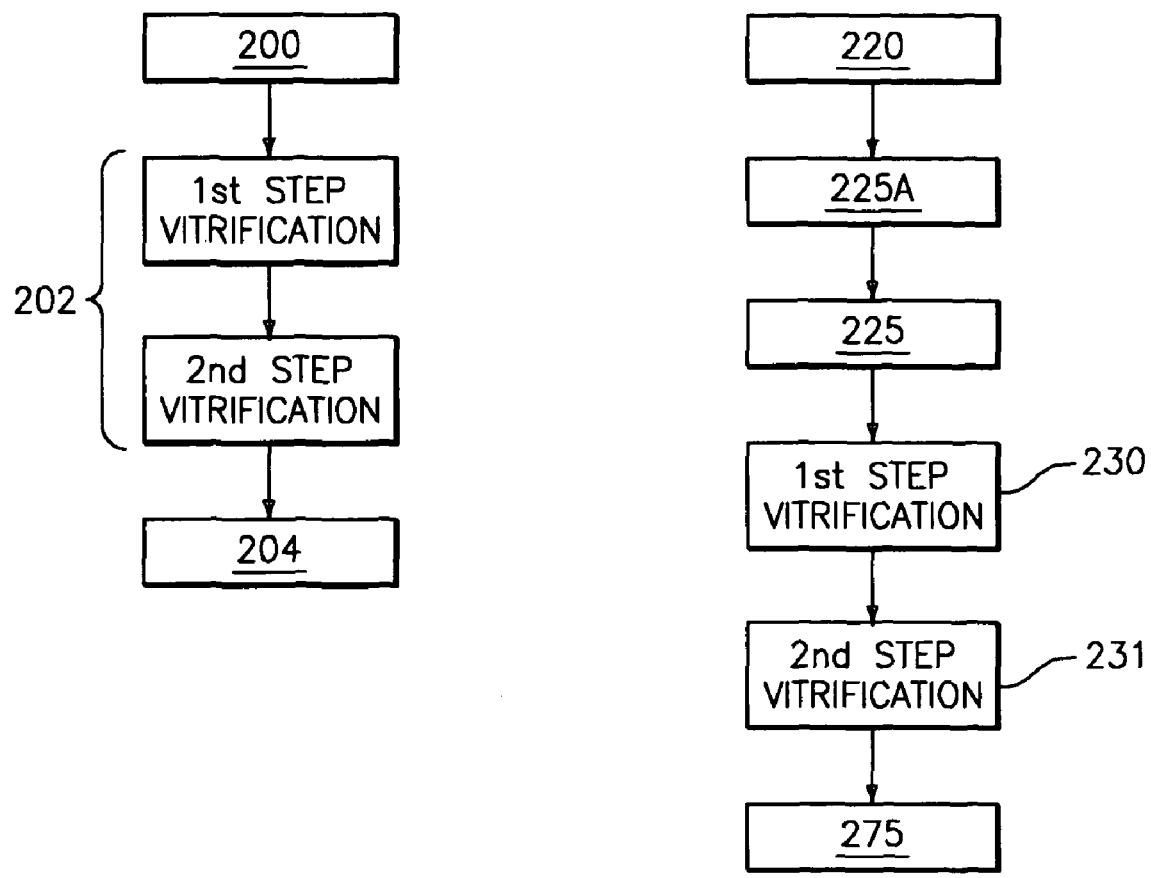
FIG. 2 is a flow chart showing methods for application of the invention in an embryo vitrification process.

Referring now to FIG. 2, there is shown a similar procedure for freezing or vitrifying specimens such as embryos, stem cells or oocytes. In the prior art method, the specimens, such as embryos or oocytes to be cryopreserved by freezing or vitrification are cultured in a culturing media 200. This occurs in an incubator environment. The embryos are selected for cryopreservation and then put through the vitrification or freezing process in specific cryoprotectorant (CP) media solutions 202. Typically in the first vitrification step, the media will include two cryoprotectorants which will each provide 7.5% of the first step medium. Then in the second vitrification step, the cryoprotectorants will each provide 15% of the second step medium. After they have been thus prepared for vitrification in the are then moved to storage in a liquid nitrogen tank 204. The specimens will remain in the tank 204 until needed to be thawed and used.

The method of this invention includes a specially designed media in the sequence to provide the embryos with much needed components before they enter the vitrification process. The embryos are cultured in an embryo culture media 220, before cryopreservation. The embryos are moved from the generic culture medium into a preparation/rejuvenation medium 225A which contains the combination of ingredients, described above and is devoid of HEPES or MOPS. This special solution contains additional ingredients useful in preparing the specimen for cryopreservation. The embryos are then moved into a second preparation/rejuvenation medium 225B which does contain, HEPES or MOPS. Including HEPES or MOPS, a bicarbonate, allows the embryos to be handled outside the incubator environment, and including HEPES or MOPS allows the user to prepare the embryos inside of the incubator environment for a longer period of time. The embryos are then placed in the sequential vitrification solutions 230 and 231, and then stored in liquid nitrogen tank 275.

Referring now to the tables, Table 1 shows the changes made to a basic media formulation A. This table shows what is a generic medium solution that has been successful in developing embryos through to the cleavage and blastocyst stage of development. This table shows the majority of ingredients used in this proven medium. The combination of pyruvates, glucose and lactate in the rejuvenation solution will outperform the conventional media in the post thawing process. Added to the proven media formulations are varying amounts of fatty acids, vitamins, antioxidants and globulins.

The term "amino acid" as used herein, refers to amino acids or their derivatives. Examples of such amino acids include L-alamine, glycine, L-alanine, L-arginine HCL, L-asparagine, L-cysteine, L-aspartic acid, L-glutamic acid, glycyl-glutamine, L-phenylalanine, L-histidine, L-isoleucine, L-lysine HCL, L-leucine, L-proline, L-serine, L-threonine, L-tryptophan, L-tyrosine, and L-valine.

In modifying the basic medium ingredients, glucose is increased ten fold from 0.036 to 0.18 g/L. Lactate is decreased from 1.12 to 0.56 gg/L. Pyruvate is increased from 0.022 to 0.030 g/L. The levels may vary slightly and acceptable levels of glucose may be from 0.20 to 0.40 g/L; lactate may vary from 0.20 to 1.20 g/L; and pyruvates may vary from 0.005 to 0.030 g/L.

The medium of this invention includes the addition of fatty acids, lipioc acid in a concentration of from 0.000004 to 0.0000012 g/L, with a preferred amount of 0.000008 g/L; and linoleic acid in a concentration of from 0.000002 to 0.000008, with a preferred amount of 0.00005 g/L. The fatty acids may be supplemented with similar performance fatty acids.

The invention includes the addition of vitamins, alpha tocopheral acetate in a concentration of from 0.00025 to 0.00075 g/L, with a preferred embodiment of 0.0005 g/L, ascorbic acid phosphate in a concentration of from 0.001 to 0.01, with a preferred amount of 0.0025 g/L. Menadione K3 in a concentration of from 0.00005 to 0.0005, with a preferred amount of 0.0001 g/L. Vitamin K2 in a concentration of from 0.00005 to 0.0005, with a preferred amount of 0.0001 g/L; globulin may be added separately or in a subcomponent such as HAS and globulin. The vitamins may be supplemented with similar performance vitamins.

Table 2 compares some of the media considered in the prior art example of FIG. 1. Table 2 shows the more common "generic" media solutions in the marketplace and their published concentration of the ingredients glucose, sodium and sodium lactate. This includes those common in embryo development and culturing. Table 2 shows that P1, a common culture medium, which would be used as the generic medium of FIG. 1, has no glucose; three times the amount of sodium pyruvates; and more than four times the amount of sodium lactate. In Table 2 there is shown that most concentrations of sodium lactate are at least two times the level of the resucitation culture medium of this invention. This embodiment of the resucitation culture medium of this invention has balanced and added ingredients to best culture and allow the embryos to revive after thawing.

The invention includes the addition of fatty acids, lipioc acid in a concentrations of from 0.000004 to 0.0000012 g/L, with a preferred concentration of 0.000008 g/L, and linoleic acid in concentrations of from 0.000002 to 0.000008 g/L, with a preferred concentration of 0.00005 g/L. These fatty acids may be supplemented with similar performance fatty acids.

Since many changes and variations of the disclosed embodiment of the invention may be made without departing from the inventive concept, it is not intended to limit the invention except as required by the appended claims.

What is claimed is:

1. A method of freezing or vitrifying an embryo or oocyte specimen or specimens for storage in liquid nitrogen, said method comprising;
   a) removing said specimen or specimens from a culture medium and placing said specimen or specimens in a first rejuvenation medium comprising effective amounts of glucose, pyruvate, amino acids, vitamins K5 and C, antioxidants, and fatty acids sufficient to supply the specimen or specimens with chemical ingredients and uptake requirements required to recover and prosper during the cryopreservation process, said first rejuvenation medium being operative to supply nutrients which will protect from depletion and damage to said specimen or specimens and its or their mitochondria, spindles, and structural features during cryopreservation, said first rejuvenation medium being devoid of HEPES or MOPS;
   b) removing said specimen or specimens from said first rejuvenation medium and placing said specimen or specimens into a second rejuvenation medium comprising effective amounts of glucose, pyruvate, amino acids, vitamins K5 and C, antioxidants, and fatty acids sufficient to supply the specimen or specimens with chemical ingredients and uptake requirements required to recover and prosper during the cryopreservation process, said second rejuvenation medium being operative to supply nutrients which will protect from depletion and damage to said specimen or specimens and its or their mitochondria, spindles, and structural features during cryopreservation, said second rejuvenation medium including HEPES or MOPS;
   c) removing said specimen or specimens from said second rejuvenation medium and placing said specimen or specimens in a first solution comprising a first amount of one or more cryoprotectants;
   d) removing said specimen or specimens from said first solution and placing said specimen or specimens in a second solution comprising a second amount of one or more cryoprotectants which is greater than said first amount of cryoprotectant in step c); and
   e) removing said specimen or specimens from said second solution and placing said specimen or specimens in liquid nitrogen.

2. The method of claim 1, wherein said fatty acids include lipoic acid and linoleic acid.

3. The method of claim 2, wherein said lipoic acid is present in a concentration range of about 0.000004 g/L to about 0.000008 g/L.

4. The method of claim 2, wherein said linoleic acid is present in a concentration range of about 0.0000025 g/L to about 0.000010 g/L.

5. A method of freezing or vitrifying an embryo or oocyte specimen for storage in liquid nitrogen, said method comprising;
   a) removing said specimen from a culture medium and placing said specimen in a first rejuvenation medium comprising effective amounts of glucose, pyruvate, amino acids, vitamins K and C, antioxidants, and fatty acids sufficient to supply the specimen with chemical ingredients and uptake requirements required to recover and prosper during the cryopreservation process, said first rejuvenation medium being operative to supply nutrients which will protect from depletion and damage to said specimen and its mitochondria, spindles, and structural features during cryopreservation, said first rejuvenation medium being devoid of HEPES or MOPS;
   b) removing said specimen from said first rejuvenation medium and placing said specimen into a second rejuvenation medium comprising effective amounts of glucose, pyruvate, amino acids, vitamins K and C, antioxidants, and fatty acids sufficient to supply the specimen with chemical ingredients and uptake requirements required to recover and prosper during the cryopreservation process, said second rejuvenation medium being operative to supply nutrients which will protect from depletion and damage to said specimen and its mitochondria, spindles, and structural features during cryopreservation, said second rejuvenation medium including HEPES or MOPS;
   c) removing said specimen from said second rejuvenation medium and placing said specimen in a first solution comprising a first amount of one or more cryoprotectants;

d) removing said specimen from said first solution and placing said specimen in a second solution comprising a second amount of one or more cryoprotectants which is greater than said first amount of cryoprotectant in step c); and e) removing said specimen from said second solution and placing said specimen in liquid nitrogen.

* * * * *